United States Patent
Xu et al.

(10) Patent No.: US 10,203,527 B2
(45) Date of Patent: Feb. 12, 2019

(54) QUANTUM DOT FILM AND DISPLAY DEVICE

(71) Applicants: BOE Technology Group Co., Ltd., Beijing (CN); Chengdu BOE Optoelectronics Technology Co., Ltd., Chengdu (CN)

(72) Inventors: Yuanjie Xu, Beijing (CN); Weiyun Huang, Beijing (CN); Yang Wang, Beijing (CN)

(73) Assignees: BOE TECHNOLOGY GROUP CO., LTD., Beijing (CN); CHENGDU BOE OPTOELECTRONICS TECHNOLOGY CO., LTD., Chengdu (CN)

( * ) Notice: Subject to any disclaimer, the term of this patent is extended or adjusted under 35 U.S.C. 154(b) by 0 days.

(21) Appl. No.: 15/533,098

(22) PCT Filed: Jun. 22, 2016

(86) PCT No.: PCT/CN2016/086675
§ 371 (c)(1),
(2) Date: Jun. 5, 2017

(87) PCT Pub. No.: WO2017/161714
PCT Pub. Date: Sep. 28, 2017

(65) Prior Publication Data
US 2018/0059441 A1    Mar. 1, 2018

(30) Foreign Application Priority Data
Mar. 22, 2016    (CN) .......................... 2016 1 0169476

(51) Int. Cl.
*H01L 31/00*    (2006.01)
*A61L 2/00*    (2006.01)
(Continued)

(52) U.S. Cl.
CPC ............ *G02F 1/017* (2013.01); *A61L 2/0047* (2013.01); *G02F 1/1335* (2013.01);
(Continued)

(58) Field of Classification Search
CPC ............... G02F 1/017; G02F 1/133617; G02F 1/133621; G02F 2001/01791;
(Continued)

(56) References Cited

U.S. PATENT DOCUMENTS 7,122,827 B2 * 10/2006 Alizadeh ................ B82Y 20/00
                                                        257/17
7,888,700 B2    2/2011 Kahen
(Continued)

FOREIGN PATENT DOCUMENTS

CN    1858633 A    11/2006
CN    1977999 A    6/2007
(Continued)

OTHER PUBLICATIONS

Himwas et al. "Thermal stability of the deep ultraviolet emission from AlGaN/AlN Stranski-Krastinov quantum dots", 2012, Applied Physics Letter, vol. 101, 241914-1-241914-5 (published Dec. 12, 2012).*
(Continued)

*Primary Examiner* — Nikolay Yushin
(74) *Attorney, Agent, or Firm* — Westman, Champlin & Koehler, P.A.

(57) ABSTRACT

A quantum dot film and a display device are disclosed herein. The quantum dot film includes a substrate and at least one ultraviolet quantum dot disposed in the substrate and capable of emitting ultraviolet rays having a wavelength in a range of 190 to 280 nm.

10 Claims, 4 Drawing Sheets

(51) Int. Cl.
*G02F 1/017* (2006.01)
*G02F 1/1335* (2006.01)
*H01L 31/054* (2014.01)

(52) U.S. Cl.
CPC ...... *H01L 31/054* (2014.12); *G02F 1/133617* (2013.01); *G02F 2001/01791* (2013.01)

(58) Field of Classification Search
CPC ... G02F 1/1335; G02F 1/13361; B82Y 20/00; B82Y 10/00; B82Y 40/00; A61L 2/0047; A61L 2/08; A61L 2/084; H01L 31/054; H01L 31/035218; H01L 31/18; H01L 31/0352; H01L 31/06; H01L 31/08
See application file for complete search history.

(56) References Cited

U.S. PATENT DOCUMENTS

| | | | |
|---|---|---|---|
| 7,995,871 B2 | 8/2011 | Guerra | |
| 8,675,167 B2* | 3/2014 | Jang | B82Y 20/00 349/163 |
| 9,030,108 B2* | 5/2015 | Deak, Sr. | H05B 33/0803 257/17 |
| 9,529,133 B2 | 12/2016 | Yang et al. | |
| 2005/0082543 A1* | 4/2005 | Alizadeh | B82Y 20/00 257/79 |
| 2008/0217602 A1 | 9/2008 | Kahen | |
| 2010/0208172 A1* | 8/2010 | Jang | B82Y 20/00 349/71 |
| 2013/0293123 A1* | 11/2013 | Deak, Sr. | H05B 33/0803 315/186 |
| 2014/0050882 A1* | 2/2014 | Tsai | B32B 3/10 428/131 |
| 2016/0033714 A1 | 2/2016 | Liu | |
| 2016/0146999 A1 | 5/2016 | Yang et al. | |

FOREIGN PATENT DOCUMENTS

| | | |
|---|---|---|
| CN | 101681956 A | 3/2010 |
| CN | 102786765 A | 11/2012 |
| CN | 103172275 A | 6/2013 |
| CN | 203179892 U | 9/2013 |
| CN | 103775919 A | 5/2014 |
| CN | 104409592 A | 3/2015 |
| CN | 105388668 A | 3/2016 |
| WO | 2012/057431 A1 | 5/2012 |

OTHER PUBLICATIONS

International Search Report and Written Opinion for International Application No. PCT/CN2016/086675, dated Dec. 12, 2016, 9 pages.
English translation of International Search Report and Written Opinion for International Application No. PCT/CN2016/086675, 10 pages.
First Office Action, including Search Report, for Chinese Patent Application No. 201610169476.7, dated May 3, 2018, 12 pages.
C. Himwas et al., "Thermal stability of the deep ultraviolet emission from AlGaN/AlN Stranski-Krastanov quantum dots," Applied Physics Letters 101, 241914 (2012), Dec. 12, 2012, 5 pages.

* cited by examiner

QUANTUM DOT FILM AND DISPLAY DEVICE

CROSS-REFERENCE TO RELATED APPLICATION

This application is a Section 371 National Stage Application of International Application No. PCT/CN2016/086675, filed on 22 Jun. 2016, which has not yet published, and claims priority to Chinese Patent Application No. 201610169476.7 filed on Mar. 22, 2016, entitled "QUANTUM DOT FILM AND DISPLAY DEVICE", in the State Intellectual Property Office of China, the disclosures of which are incorporated in entirety herein by their reference.

BACKGROUND

Technical Field

Embodiments of the present disclosure relate to a field of display technology, and more particularly, to a quantum dot film and a display device.

Description of the Related Art

Currently, touch display screens are widely used in mobile communication, tablet computer, camera, satellite navigation, medical equipment and other display applications. But there are also some problems. For example, the touch display screen is generally used at a very high frequency, so that it easily becomes a medium transmitting virus, bacteria and other microorganism. Such a problem is particularly prominent in many public places and medical and health care places where it raises a strict requirement on bacteria and virus. Therefore, it becomes a non-negligible task how to ensure a clean and sanitary screen in the touch display screen.

Quantum dots may also be referred to be as nanocrystalline, which is a kind of nanoparticles composed of II-VI or III-V (group) elements. The particle size of the quantum dots is generally in a range of 1 to 20 nm. Since electrons and holes undergo quantum confinement effect, the continuous energy band structure becomes discrete energy level structures with molecular characteristics, and then they can emit fluorescence after excitation. In the prior art, quantum dots have been applied in the manufacture of the display screen. Regardless of a quantum dot film used in a backlight module or a color filter, the main principle thereof is to use quantum dots to emit three-color (i.e., being or having red, green and blue (RGB)) lights. However, the quantum dot film does not have a sterilization effect In view of the above, the quantum dot film of the touch display screen in the prior art currently does not have a sterilization effect. Moreover, the touch display screen can easily become a medium transmitting virus, bacteria and other microorganism due to a high frequency of use. Therefore, it becomes a noticeable task how to ensure a clean and sanitary screen in the touch display screen.

SUMMARY

It is an object of the present disclosure to provide a quantum dot film and a display device, so as to at least partially solve the problem that the quantum dot film of the touch display screen in the prior art does not have a sterilization effect.

According to an aspect of the present disclosure, there is provided a quantum dot film, comprising:
a substrate; and
at least one ultraviolet quantum dot disposed in the substrate and capable of emitting ultraviolet rays having a wavelength in a range of 190 to 280 nm.

In an embodiment, the quantum dot film further comprises a plurality of R quantum dots, G quantum dots and B quantum dots distributed in the substrate and capable of emitting three-color red, green and blue lights respectively.

In an embodiment, the R quantum dots, the G quantum dots and the B quantum dots are uniformly arranged layer by layer in a thickness direction of the quantum dot film.

In an embodiment, the at least one ultraviolet quantum dot is of a single layer structure in which the ultraviolet quantum dots are uniformly arranged.

In an embodiment, the at least one ultraviolet quantum dot is located above or below all layers where the R quantum dots, the G quantum dots and the B quantum dots are located, or in any one of the layers where the R quantum dots, the G quantum dots and the B quantum dots are located, or between any two adjacent ones f the layers where the R quantum dots, the G quantum dots and the B quantum dots are located.

In an embodiment, projections of occupying regions of the R quantum dots, the G quantum dots and the B quantum dots in the substrate in a direction perpendicular to the thickness direction of the quantum dot film do not overlap with each other, and adjacent two ones of the occupying regions of the R quantum dots, the G quantum dots and the B quantum dots are spaced apart by a black matrix.

In an embodiment, the at least one ultraviolet quantum dot is distributed in all or some of the occupying regions.

In an embodiment, the ultraviolet rays emitted by the at least one ultraviolet quantum dot have a wavelength in a range of 200 to 275 nm.

According to another aspect of the present disclosure, there is provided a display device, comprising the quantum dot film described above.

In an embodiment, the quantum dot film is used as a color filter module or a backlight module, and the quantum dot film comprises R quantum dots, G quantum dots and B quantum dots capable of emitting three-color red, green and blue lights respectively.

In an embodiment, the display device further comprises an antibacterial film.

In an embodiment, the antibacterial film forms an outermost film layer of the display device In an embodiment, the antibacterial film is located within the display device, and an insulation layer for insulating the antibacterial film from other film layers in the display device is provided in the display device.

In an embodiment, the antibacterial film has a thickness in a range of 50 to 500 nm.

In an embodiment, a ratio of energy of the ultraviolet rays of a wavelength in a range of 190 to 280 nm to energy of white light emitted by the display device is 2% to 4% higher than a ratio of energy of ultraviolet rays of a wavelength in a range of 190 to 280 nm to energy of white light in sunlight.

DETAILED DESCRIPTION OF PREFERRED EMBODIMENTS

The technical solutions of embodiments of the present disclosure will be clearly and thoroughly described with reference to the accompanying drawings in the embodiments of the present disclosure. It will be apparent that the described embodiments are only part of all embodiments of the present disclosure, but not exhaustive. All other embodiments obtained by those skilled in the art based on the embodiments of the present disclosure without creative work fall within the scope of the present disclosure.

An embodiment of the present disclosure provides a quantum dot film capable of emitting short-wave ultraviolet rays (UVC or ultraviolet rays of C band). Such quantum dot film may be applied in any cases where the quantum dot film is intended to be excited to emit ultraviolet rays (UVC), including a conventional OLED display screen, a liquid crystal display screen, a quantum dot screen and so on.

Figure 1:
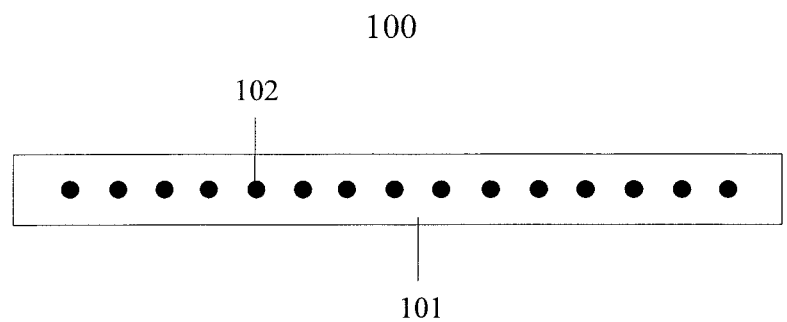
FIG. 1 is a structural schematic view of a quantum dot film according to an embodiment of the present disclosure.

FIG. 1 is a structural schematic view of a quantum dot film 100 according to an embodiment of the present disclosure. The quantum dot film 100 includes a substrate 101 and at least one ultraviolet quantum dot 102 disposed or dispersed in the substrate 101 and capable of emitting ultraviolet rays 105 (shown in FIG. 4) of C band (UVC). In the illustrated examples, a plurality of ultraviolet quantum dots 102 are always taken as an example. It will be apparent to those skilled in the art that the number of the ultraviolet quantum dots 102 may be specifically set as desired.

Figure 4:
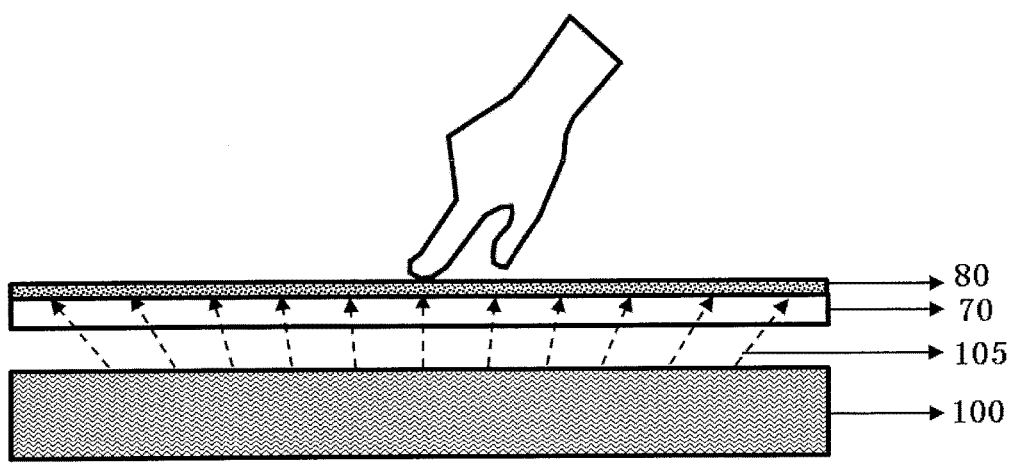
FIG. 4 is a schematic view of showing a working principle of the quantum dot film as shown in FIG. 1 when being touched.

Further, as shown in FIG. 4, the quantum dot film 100 is located at the bottom of a display device, and the ultraviolet quantum dots 102 therein emit ultraviolet rays 105 having a wavelength in a range of 190 to 280 nm. At the touch side by a hand (as shown), there is a protection plate 70 and an antibacterial film 80 located onto the protection plate 70.

The ultraviolet sterilization principle is in that DNA (desoxyribonucleic acid) structures of the microorganism are destructed or changed by ultraviolet radiation so that the bacteria immediately dies and cannot reproduce progeny, to achieve a purpose of sterilization. Generally, a sterilization effect may be achieved after UVC radiation about 1 second to 2 seconds. The ultraviolet light is divided into A band radiation, B band radiation and C band radiation (respectively referred to as UVA, UVB and UVC), having respective wavelength ranges of 400 to 315 nm, 315 to 280 nm, 280 to 190 nm. Among them, UVA and UVB are harmful to human body, while the ultraviolet rays of C band is used to implement sterilization, and the ultraviolet rays of C band can kill bacteria, virus, mold, single cell algae and other microorganisms while being harmless to the human body. It should be noted that the ultraviolet having a wavelength of less than 380 nm is not visible. Thus, since the ultraviolet quantum dots capable of emitting UVC are incorporated into the quantum dot film in the present disclosure, the display screen may be sterilized when the screen displays. Additionally, since the quantum dot film is generally located in the display screen, the sterilization effect and function thereof is more stable, but will not decrease with the service time.

If the ultraviolet rays of C band (UVC) has a wavelength of 200 to 275 nm, the sterilization effect is strongest and it is harmless to the human body. Therefore, the use of this wavelength range can not only ensure the display quality, but also the health of the human body.

In the prior art, the quantum dot film mainly includes quantum dots capable of emitting three-color (i.e., red, green and blue RGB) lights. In the present disclosure, in addition to the ultraviolet quantum dots, the quantum dot film may also be combined with the quantum dots emitting three-color (i.e., red, green and blue RGB) lights in the prior art.

Figure 2:
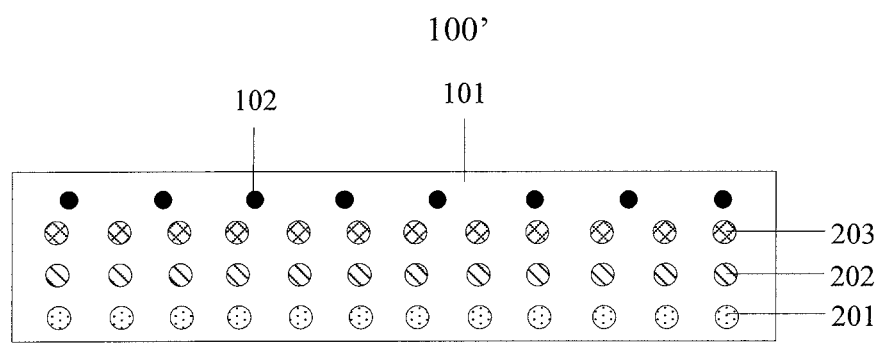
FIG. 2 is a structural schematic view of a quantum dot film including R quantum dots, G quantum dots, B quantum dots and ultraviolet quantum dots according to another embodiment of the present disclosure.

FIG. 2 is a structural schematic view of a quantum dot film 100' including R quantum dots, G quantum dots, B quantum dots and ultraviolet quantum dots according to another embodiment of the present disclosure. The quantum dot film 100' further includes a plurality of R quantum dots 201, G quantum dots 202 and B quantum dots 203 dispersed or distributed in the substrate 101 and capable of emitting three-color red, green and blue lights respectively. In FIG. 2, the black balls represent the ultraviolet quantum dots, and FIG. 2 is just a diagram showing one kind of possibly positional distribution relationship of the ultraviolet quantum dots 102 and the R quantum dots 201, the G quantum dots 202 and the B quantum dots 203, but it does not mean that there is only such one arrangement form. Next, two possible positional distribution relationships of the ultraviolet quantum dots 102 and the R quantum dots 201, the G quantum dots 202 and the B quantum dots 203 will be introduced.

Firstly, the three R, G, B quantum dots are arranged layer by layer in a thickness direction of the quantum dot film 100'.

The R quantum dots 201, the G quantum dots 202 and the B quantum dots 203 are uniformly arranged layer by layer. As shown in FIG. 2, the R quantum dots 201, the G quantum dots 202 and the B quantum dots 203 each form a uniform layer, and the G quantum dots are located between the R quantum dots and the B quantum dots.

As for the ultraviolet quantum dots 102 according to the embodiments of the present disclosure, it is not intended to limit the detailed arrangement positions of them. In an embodiment, the ultraviolet quantum dots 102 are arbitrarily distributed in the quantum dot film. Alternatively, the ultraviolet quantum dots 102 are of a layer structure in which the ultraviolet quantum dots are uniformly arranged. In a particular embodiment, the ultraviolet quantum dots 102 may be arbitrarily distributed in the quantum dot film, for example, they are located above all the layers as shown, or they are located below all the layers. Alternatively, the ultraviolet quantum dots 102 is located in any one of a layer of R quantum dots, a layer of G quantum dots and a layer of B quantum dots, or between two layers as described above.

Further, the ultraviolet quantum dots 102 may uniformly arranged in a layer, as shown in FIG. 2.

Secondly, the three R, G, B quantum dots are arranged in different regions in the same layer.

Figure 3:
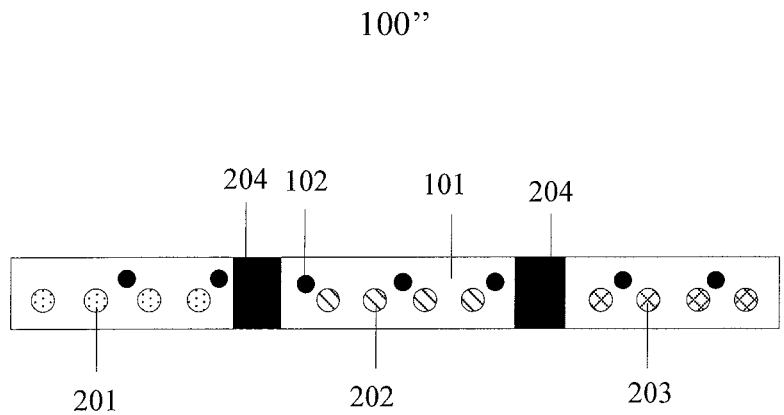
FIG. 3 is a structural schematic view of another quantum dot film including R quantum dots, G quantum dots, B quantum dots and ultraviolet quantum dots according to a further embodiment of the present disclosure.

FIG. 3 is a structural schematic view of another quantum dot film 100" including R quantum dots, G quantum dots, B quantum dots and ultraviolet quantum dots according to a further embodiment of the present disclosure. Projections of occupying regions of the R quantum dots 201, the G quantum dots 202 and the B quantum dots 203 in the substrate 101 in a direction perpendicular to the thickness direction of the quantum dot film 100" do not overlap with each other, and adjacent two ones of the occupying regions of the R quantum dots, the G quantum dots and the B quantum dots are spaced apart by a black matrix 204. In FIG. 3, the R quantum dots 201, the G quantum dots 202 and the B quantum dots 203 are respectively distributed in different regions of the substrate 101, and the occupying regions of various kinds of quantum dots do not overlap with each other. In the figure, the black rectangle represents the black matrix 204 for separating the adjacent occupying regions.

As for the ultraviolet quantum dots 102 according to the embodiments of the present disclosure, it is not intended to limit the detailed arrangement positions of them. The ultraviolet quantum dots 102 are distributed in all or some of the occupying regions of various kinds of quantum dots. In a particular embodiment, the ultraviolet quantum dots 102 are distributed in all of the occupying regions of various kinds of quantum dots, or the ultraviolet quantum dots 102 are distributed in some of the occupying regions of various kinds of quantum dots, which may be set as desired.

The two above arrangements of the three R, G, B quantum dots are only two feasible solutions, but it is not intended to limit the present disclosure. The other specific arrangements may be referred to the arrangements of the three R, G, B quantum dots contained in the quantum dot film in the prior art.

When the embodiments of the present disclosure are implemented, it is necessary for the ultraviolet quantum dots 102 according to the embodiments of the present disclosure to emit ultraviolet rays of C band (UVC), and it needs to use quantum dot materials with absorption peak in other ray bands and fluorescence emission peak in UVC waveband. The specific materials for manufacturing the ultraviolet quantum dots, the specific methods for manufacturing the quantum dots and the dimension of the quantum dots may refer to the solutions, in which the quantum dots are allowed to emit ultraviolet light, in the prior art. Thus, they are described herein any more.

The specific arrangement position of the ultraviolet quantum dots 102 may be set as desired, and it is not limited to the arrangements provided above. For example, the ultraviolet quantum dots 102 may be uniformly arranged in the quantum dot film, or may be provided only at periphery of the display device, or at four sides or corners of the display device.

According to the same inventive concept, the embodiments of the present disclosure also provide a display device including the above quantum dot film according to the embodiments of the present disclosure. The display device may be a mobile phone, a tablet computer, a television set, a display, a notebook computer, a digital photo frame, a navigator and any other products or components having a display function. Other integral parts for the display device may be provided by those skilled in the art, therefore they are not described and they are not intended to limit the present disclosure. The display device may be implemented with reference to the embodiments of the above quantum dot film, which is not described herein again.

When the quantum dot film in the display device includes R quantum dots, G quantum dots and B quantum dots capable of emitting three-color red, green and blue lights respectively, the quantum dot film is used as a color filter module or a backlight module.

When the embodiments of the present disclosure are implemented, the color filter module or backlight module in the display device may be generally replaced by the quantum dot film including the R quantum dots, the G quantum dots and the B quantum dots capable of emitting three-color red, green and blue lights which are placed with different arrangements. In the quantum dot film according to the embodiments of the present disclosure, ultraviolet quantum dots capable of emitting UVC may be provided in the R quantum dots, the G quantum dots and the B quantum dots, so as to function to sterilize the display screen when the screen displays, while ensuring the display quality and the health of the human body. Thus, the quantum dot film according to the embodiments of the present disclosure may act as a color filter module or backlight module in the display device.

Figure 5:
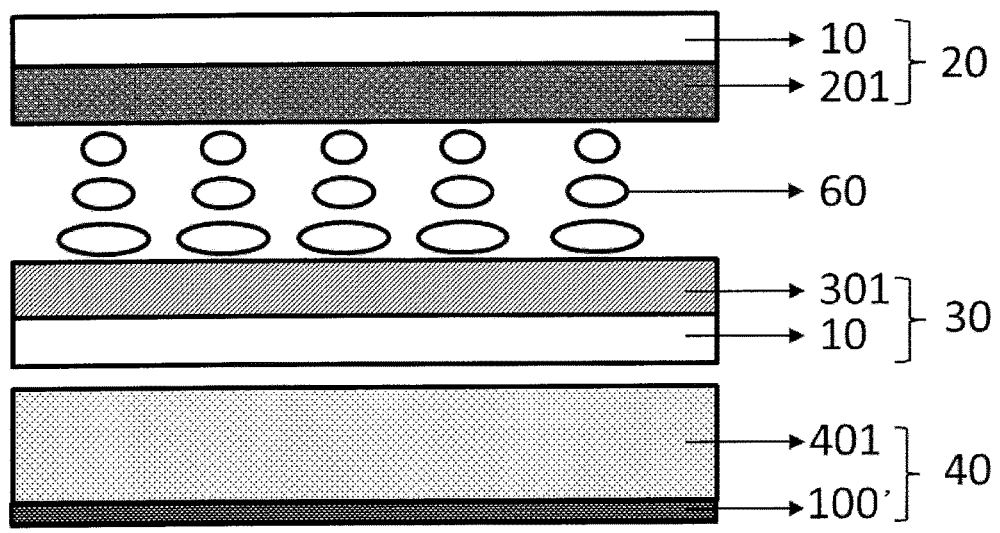
FIG. 5 is a structural schematic view of the quantum dot film as shown in FIG. 2 in a backlight module in a liquid crystal display device.
Figure 6:
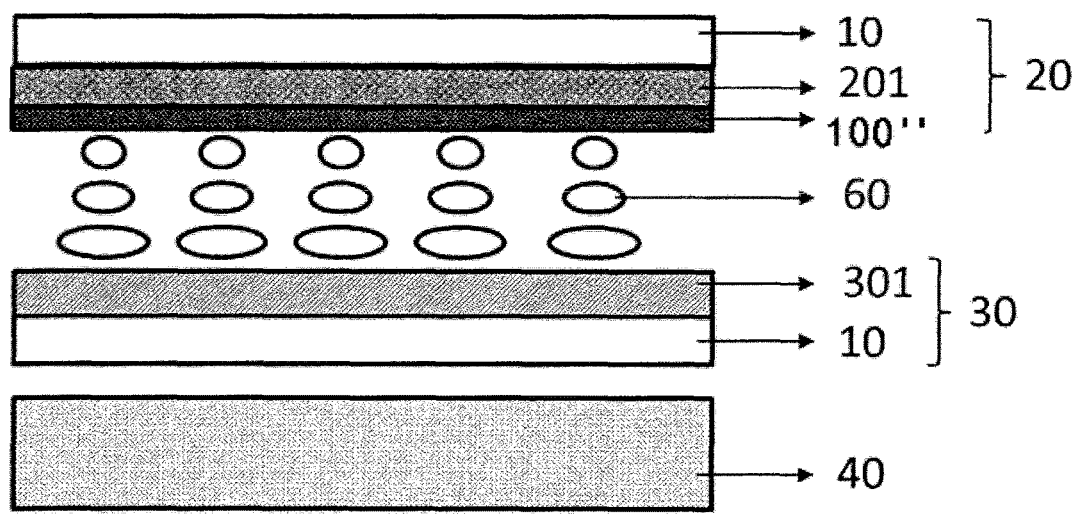
FIG. 6 is a structural schematic view of the quantum dot film as shown in FIG. 3 in a color filter substrate in a liquid crystal display device.
Figure 7:
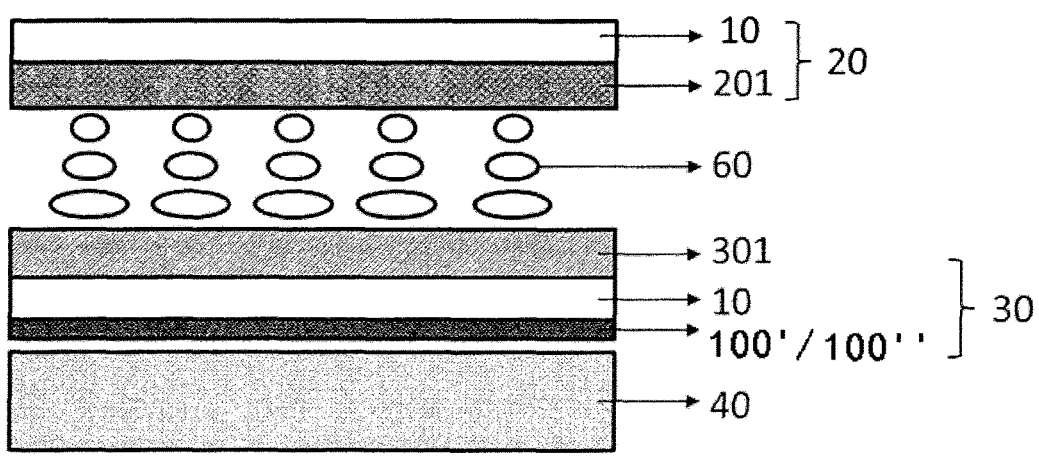
FIG. 7 is a structural schematic view of the quantum dot film as shown in FIG. 1 provided onto a bottom surface of an array substrate in a liquid crystal display device and FIG. 8 is a structural schematic view of the quantum dot film as shown in FIG. 2 in a backlight module in a liquid crystal display device with an antibacterial film at the top thereof.

That is to say, the specific arrangement position of the quantum dot film including the ultraviolet quantum dots, the R quantum dots, the G quantum dots and the B quantum dots according to the embodiments of the present disclosure may refer to the arrangement of the quantum dot film in the prior art. For example, it may be applied in a backlight module (as shown in FIG. 5), an array substrate (as shown in FIG. 7) or a color filter substrate (as shown in FIG. 6), to achieve a light emitting display effect of the quantum dots. The specific implementation for the ultraviolet quantum dots to emit light may refer to the modes of the quantum dots for emitting ultraviolet light or other monochromatic light in the prior art.

FIG. 5 is a structural schematic view of the quantum dot film as shown in FIG. 2 located in a backlight module in a liquid crystal display device. As shown in FIG. 5, the quantum dot film 100' is used to as a part a light source part of a backlight module 40, and located below other parts of the backlight module 40. An array substrate 30, a liquid crystal layer 60 and a color filter substrate 20 are arranged in sequence above the backlight module 40. Further, the array substrate 30 includes a base substrate 10 and function parts 301 of the array substrate 30 onto the base substrate 10. Similarly, the color filter substrate 20 includes a base substrate 10 and function parts 201 of the color filter substrate 20 below the base substrate 10.

FIG. 6 is a structural schematic view of the quantum dot film as shown in FIG. 3 in a color filter substrate in a liquid crystal display device. As shown in FIG. 6, the liquid crystal display device includes a backlight module 40, an array substrate 30, a liquid crystal layer 60 and a color filter substrate 20 arranged in sequence from bottom to top. Most parts shown in FIG. 6 are similar those as shown in FIG. 5, and the description about them are omitted herein. One difference of FIG. 6 from FIG. 5 is that the quantum dot film is one shown in FIG. 3 and provided between the function parts 201 of the color filter substrate 20 and the liquid crystal layer 60. In this way, such quantum dot film 100' is used to replace RGB color film in the function parts 201.

FIG. 7 is a structural schematic view of the quantum dot film as shown in FIG. 1 provided onto a bottom surface of an array substrate in a liquid crystal display device. The quantum dot film as shown in FIG. 7 is identical to the one shown in FIG. 2 or 3, but provided onto the bottom surface of the base substrate 10 of the array substrate 30. Since other parts are corresponding to those shown in FIG. 5 or 6, the description to them is omitted herein.

In order to solve the problem that a screen of a touch display screen is easily to be dirty and carries bacteria and virus, the present disclosure adds ultraviolet quantum dots capable of emitting UVC of a specific wavelength into the quantum dot film of the display device, thereby achieving a function of sterilization by UVC. In order to improve the sterilization effect, an antibacterial film in the prior art may be used, so as to achieve a self-cleaning and antibacterial function of the display panel. In an embodiment, the display device further includes an antibacterial film. As for the materials, dimension and manufacturing method of the antibacterial film according to the embodiments of the present disclosure, reference may be made to the antibacterial film in the prior art, as long as it forms an antibacterial film which has a sterilization ability and which has an enhanced sterilization ability under UVC irradiation, therefore, it is not intended to make too much limitation or description to the antibacterial film.

It is not intended to limit the specific position of the antibacterial film 80 according to the embodiments of the present disclosure, thus it can be located at any positions in the display device. In an embodiment, since an outer film layer of the touch display screen is in direct contact with the human hand, the antibacterial film is located at outermost of the display device or forms an outermost film layer of the display device. The antimicrobial film 80 may also be provided on a front or back face, or a side of a housing of the display device such as a mobile phone, for sterilizing and cleaning the surfaces of the display device.

Figure 8:
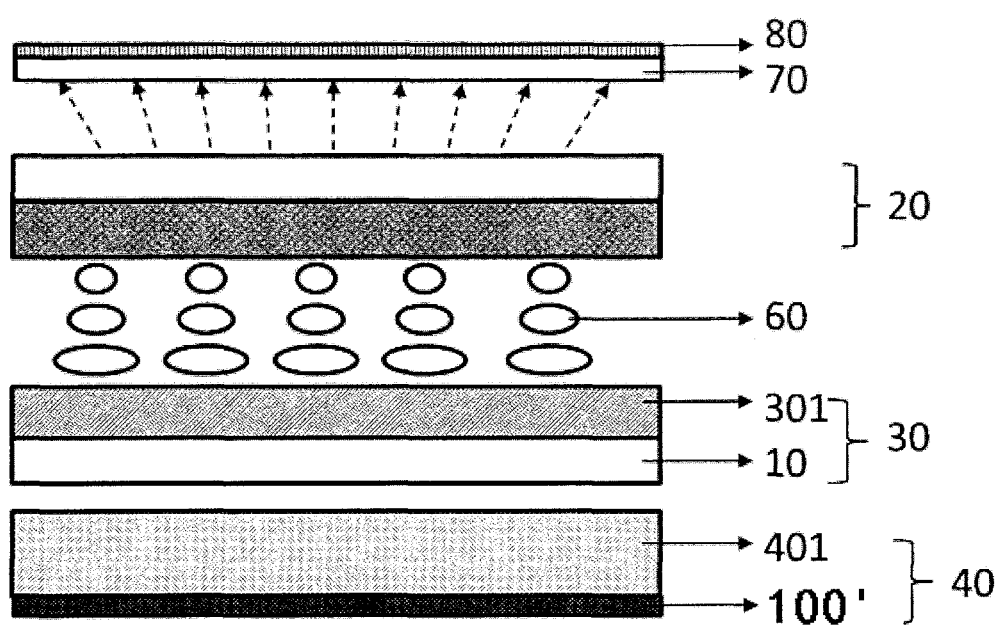

FIG. 8 is a structural schematic view of the quantum dot film as shown in FIG. 2 in a backlight module in a liquid crystal display device with an antibacterial film at the top thereof. The liquid crystal display device as shown in FIG. 8 is mostly identical to those as shown in FIG. 5, but has an antibacterial film 80 at the top of the display device. Specifically, the antibacterial film 80 is provided on a base substrate 70.

Additionally, the above antibacterial film may be provided within the display device to keep cleaning inside the display device, facilitating the protection of internal circuits and components of the display device. Further, in order not to affect normal operation of the other layers, two insulation layers may be respectively provided at the upper and lower surfaces of the antibacterial film. In an embodiment, the antibacterial film is located within the display device, and an insulation layer for insulating the antibacterial film from the other layers is provided in the display device.

When the embodiments of the present disclosure are implemented, in order not to increase the thickness of the display device, but also effective play the role of the antibacterial film, the thickness of the antimicrobial film in one example is in a range of 50 to 500 nm.

The amount of UVC emitted from the display device can be appropriately set in order to make the UVC emitted from the display device perform a good sterilization effect without affecting a normal display of the display device or causing harm to the human body. In an embodiment, a ratio of energy of the UVC to energy of white light emitted from the display device is 2% to 4% higher than a ratio of energy of the UVC to energy of white light in sunlight.

In summary, the ultraviolet quantum dots capable of emitting the ultraviolet rays of C band (UVC) are incorporated into the quantum dot film in the present disclosure, thus the display screen may be sterilized when the screen displays. Additionally, since the quantum dot film is generally located in the display screen, the sterilization effect and function will not decrease with the service time.

It will be apparent that various changes and modifications to the present disclosure may be made by those skilled in the art without departing from the spirit and scope of the present disclosure. In this way, if these changes and modifications to the present disclosure fall within the scope of the present disclosure and the equivalents thereof, then it is intended to include these changes and modifications in the present disclosure.

What is claimed is:

1. A liquid crystal display device, comprising a backlight module, an array substrate, a liquid crystal layer and a color filter substrate provided in sequence;
    wherein a quantum dot film is located in or onto one of the backlight module, the color filter substrate, and the array substrate,
    wherein the quantum dot film includes:
    a substrate,
    RGB quantum dots disposed in the substrate, wherein the RGB quantum dots are capable of emitting ultraviolet rays having a wavelength in a range of 190 nm to 280 nm to provide lights for display and the RGB quantum dots comprise R quantum dots, G quantum dots and B quantum dots capable of emitting three-color red, green and blue lights respectively; and
    a plurality of ultraviolet quantum dots disposed in the substrate, wherein the ultraviolet quantum dots are located above or below a layer where the RGB quantum dots are located and the ultraviolet rays emitted by the ultraviolet quantum dot have a wavelength in a range of 200 to 275 nm;
    wherein both the RGB quantum dots and the ultraviolet quantum dots are composed of group II-VI or group III-V nanoparticles having a size in a range of 1 to 20 nm;
    wherein a ratio of an intensity of the ultraviolet rays of a wavelength in a range of 190 to 280 nm to an intensity of white light emitted by the display device is 2% to 4% higher than a ratio of an intensity of ultraviolet rays of a wavelength in a range of 190 to 280 nm to an intensity of white light in sunlight.

2. The display device according to claim 1, wherein the quantum dot film is used as part of the color filter module, the backlight module and the array substrate.

3. The liquid crystal display device according to claim 1, wherein the antibacterial film forms an outermost film layer of the liquid crystal display device.

4. The liquid crystal display device according to claim 1, wherein the antibacterial film is located within the liquid crystal display device, and an insulation layer for insulating the antibacterial film from other film layers in the display device is provided in the display device.

5. The liquid crystal display device according to claim 1, wherein the antibacterial film has a thickness in a range of 50 to 500 nm.

6. The display device according to claim 1, further comprising an antibacterial film.

7. The liquid crystal display device according to claim 1, wherein R quantum dots, G quantum dots and B quantum dots are distributed in the substrate;
    wherein the R quantum dots, the G quantum dots and the B quantum dots are uniformly arranged layer by layer in a thickness direction of the quantum dot film.

8. The liquid crystal display device according to claim 7, wherein the at least one ultraviolet quantum dot is of a single layer structure in which the ultraviolet quantum dots are uniformly arranged, wherein the at least one ultraviolet quantum dot is located above or below all layers where the R quantum dots, the G quantum dots and the B quantum dots are located, or in any one of the layers where the R quantum dots, the G quantum dots and the B quantum dots are located, or between any two adjacent ones of the layers where the R quantum dots, the G quantum dots and the B quantum dots are located.

9. The liquid crystal display device according to claim 7, wherein projections of occupying regions of the R quantum dots, the G quantum dots and the B quantum dots in the substrate in a direction perpendicular to a thickness direction of the quantum dot film do not overlap with each other, and adjacent two ones of the occupying regions of the R quantum dots, the G quantum dots and the B quantum dots are spaced apart by a black matrix.

10. The liquid crystal display device according to claim 9, wherein the at least one ultraviolet quantum dot is distributed in all or some of the occupying regions.

* * * * *